(12) United States Patent
Fournet et al.

(10) Patent No.: US 8,344,145 B2
(45) Date of Patent: Jan. 1, 2013

(54) SALTS OF 2-SUBSTITUTED QUINOLINES

(75) Inventors: Alain Fournet, Ossages (FR); Nashira Campos Vieira, Brasilia (BR); Bruno Figadere, Saint Cheron (FR); Blandine Seon Meniel, Authon la Plaine (FR); Joël Vacus, Saint Maurice Montcouronne (FR); Philippe Loiseau, Gif-sur-Yvette (FR); Rodolphe Baudoin, Garches (FR)

(73) Assignee: Institut de Recherche pour le Developpement, Marseilles (FR)

( * ) Notice: Subject to any disclaimer, the term of this patent is extended or adjusted under 35 U.S.C. 154(b) by 0 days.

(21) Appl. No.: 12/937,878

(22) PCT Filed: Apr. 14, 2009

(86) PCT No.: PCT/FR2009/000425
§ 371 (c)(1),
(2), (4) Date: Mar. 2, 2011

(87) PCT Pub. No.: WO2009/144407
PCT Pub. Date: Dec. 3, 2009

(65) Prior Publication Data
US 2011/0144154 A1  Jun. 16, 2011

(30) Foreign Application Priority Data
Apr. 15, 2008  (FR) .................................... 08 02072

(51) Int. Cl.
*C07D 215/10* (2006.01)
*C07D 215/14* (2006.01)
(52) U.S. Cl. ...................................... 546/152; 546/182

(58) Field of Classification Search ........................ None
See application file for complete search history.

(56) References Cited

FOREIGN PATENT DOCUMENTS
WO  WO 93/07125       4/1993
WO  WO 02/057238 A1  7/2002
WO  WO 2007/007132 A1  1/2007

OTHER PUBLICATIONS

Berge et al., Pharmaceutical Salts, 66(1) J. Pharma. Sci. 1-19 (1977).*
Database CA [Online] Chemical Abstracts Service, Columbus, Ohio, US; Ciufolini, Marco A. et al: "The aza-Achmatowicz rearrangement: a route to useful building blocks for nitrogen containing structures"; XP002504178 retrieved from STN Database accession No. 1987:439567 RN= 109121-64-4 abstract -& Tetrahedron Letters, 27(42), 5085-8 Coden: Teleay; ISSN: 0040-4039, 1986, XP00204177, p. 5087, line 2 quinolium camphorsulfonate.
International Search Report and Written Opinion for International Application No. PCT/FR2009/000425, completed Sep. 1, 2009.

* cited by examiner

*Primary Examiner* — Janet Andres
*Assistant Examiner* — Timothy R Rozof
(74) *Attorney, Agent, or Firm* — Alston & Bird LLP

(57) ABSTRACT

The invention relates to salts of 2-substituted quinolines, the manufacturing method for same, and use of the same for the production of drugs. Said salts are advantageous in that the same can be obtained in crystalline form, which facilitates their implementation in the manufacture of pharmaceutical compositions.

6 Claims, 3 Drawing Sheets

Superimposition of the X-ray diffraction profiles of batches 1, 2 and 3 of camsylate salt of propyl quinoleine with batch 4 (beginning of register at 5° for this last one)

SALTS OF 2-SUBSTITUTED QUINOLINES

FIELD OF THE INVENTION

A subject matter of the invention is novel salts of 2-substituted quinolines, their process of manufacture and their use in the production of medicaments. These salts have the advantage of being able to be obtained in the form of crystals, which makes it easier to use them in the manufacture of pharmaceutical compositions.

BACKGROUND OF THE INVENTION

Substituted quinolines with varied structures have been described for their action with regard to the treatment of infections due to protozoa, such as leishmaniosis, trypanosomiasis or toxoplasmosis, and/or infections due to retroviruses, such as, for example, HIV or HTLV (WO 93/07125; WO 02/057238).

However, while some molecules among quinolines have shown an advantageous potential in the treatment of these pathologies, none has made it possible to date to result in the formulation of a medicament capable of being produced on the industrial scale.

This is because, in order to make possible such a development, a molecule must simultaneously exhibit a satisfactory in vivo pharmacological activity and a reduced toxicity but also physical and physicochemical qualities which allow it to be formulated under satisfactory conditions: ease of handling, stability over time, compatibility with the excipients and resistance to the storage conditions.

Certain physical properties are required in the case of active principles which have to be employed in medicaments provided in solid oral formulation forms. In the case in particular of medicaments intended for the treatment of tropical diseases, such as leishmaniosis and trypanosomiasis, certain medicaments have to be able to be stored under very restrictive temperature and humidity conditions without losing their effectiveness or decomposing. In addition, for economic reasons, it is desirable to be able to produce in the user countries the molecules intended for these treatments. It is thus necessary for these molecules, subjected to difficult climatic conditions, to exhibit and retain all the qualities required for the formulation of a medicament, for its manufacture on industrial devices and for its storage and its distribution in the targeted countries.

SUMMARY OF THE INVENTION

In point of fact, the inventors have found that some quinolines, the biological activity of which in the treatment of the abovementioned diseases is particularly noteworthy, exhibit the disadvantage of being difficult to handle in the formulation of medicaments, in particular medicaments for the oral route in solid formulation forms.

These quinolines are in particular those corresponding to the general formula (A):

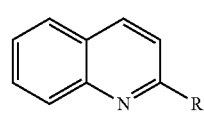

(A)

in which R represents a $C_2$-$C_5$ alkyl or alkenyl group optionally carrying one or more —OH functional groups.

This is because these molecules are provided in the form of an oil and are therefore difficult, indeed even impossible, to formulate in the form of tablets or simple hard gelatin capsules containing mixtures of powders.

Generally, in particular in tropical countries, the formulation in the solid form in tablets or hard gelatin capsules confers, on the active principles and on the medicaments which contain them, a better stability, better preservation conditions and a greater ease of use than a formulation in the liquid form. In addition, these formulation forms are simpler to produce on the manufacturing devices which are more generally available locally. In addition, the administration of hard gelatin capsules or of tablets makes it possible to avoid underdosages or overdosages more easily than liquid forms. Optional recourse to mixtures of powders available in the form of sachets or of bottles for the reconstitution at the time of use of suspensions or solutions to be taken orally makes it possible, when necessary and for high unit doses per administration, to limit the risks of chemical decomposition which might occur in ready-for-use liquid forms.

Consequently one of the objects of the invention was to be able to obtain these compounds in a solid form, preferably a crystalline form, in order to allow them to be formulated under satisfactory conditions. In addition, these compounds must retain their biological activity and their low toxicity.

These objects could be attained by virtue of the discovery of certain salts of the molecules of formula (A).

The subject matter of the invention is the salts of the molecules (A) which are molecules corresponding to the formula (I) below:

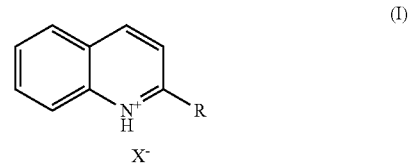

(I)

in which:
X represents the camphorsulfonate anion or the anion of 7,7-dimethyl-2-oxobicyclo[2.2.1]heptane-1-methanesulfonic acid,
R represents a linear, branched or cyclic $C_2$-$C_5$ alkyl or alkenyl group optionally carrying one or more —OH functional groups.

DETAILED DESCRIPTION OF THE INVENTION

Figure 1:
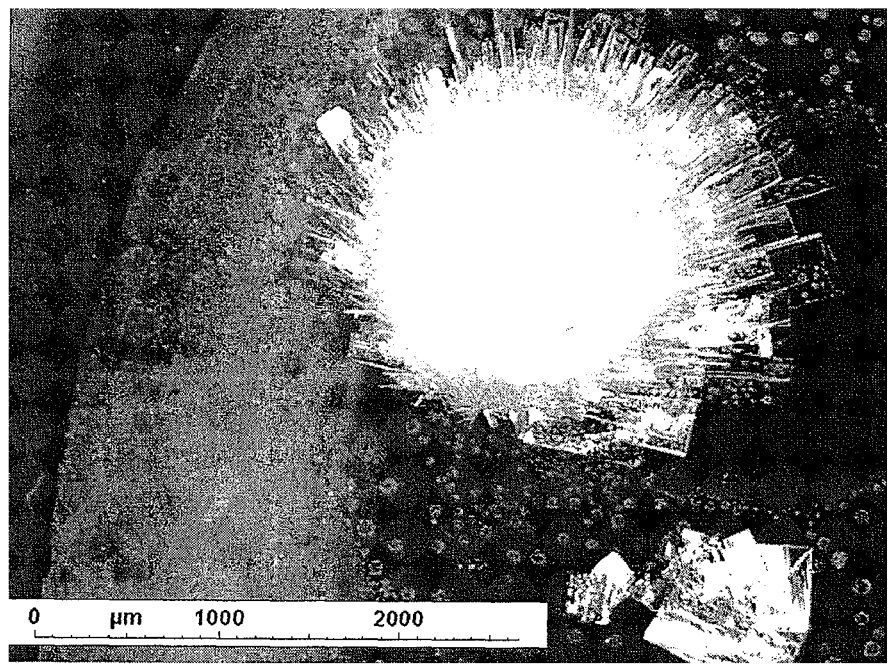
FIG. 1 is an optical microscopy photograph of crystals of 2-(n-propyl)quinoline camsylate salt in reflected light, at magnification ×40.

Mention may in particular be made, among the molecules corresponding to the above formula (I), of the camphorsulfonic acid salts of 2-(n-pentyl)quinoline,
2-(n-propyl)quinoline,
2-propenylquinoline,
2-(2-hydroxypropenyl)quinoline.

The invention is again characterized in that these molecules can be crystallized or recrystallized and thus obtained in the form of crystals which are more stable, easier to handle and easier to formulate in the form of tablets or hard gelatin capsules or powders (packaged in the form of sachets or bottles) intended in particular for the preparation at the time of use of suspensions or solutions to be taken orally.

In the case of 2-(n-propyl)quinoline, the crystalline form is characterized by the presence of the following peaks in the X-ray diffraction spectrum, measured on a diffractometer in theta-theta configuration, equipped with a copper anticathode and expressed in terms of interlattice distances d, of Bragg 2-theta angle and of relative intensity:

| 2-Theta angle (°)* | Interlattice distance d (angström)** | Relative intensity (%)*** |
|---|---|---|
| 4.463 | 19.78297 | 79.1 |
| 12.975 | 6.81756 | 89.3 |
| 14.223 | 6.22226 | 49.6 |
| 14.407 | 6.14309 | 100 |
| 17.02 | 5.20542 | 56.7 |
| 22.586 | 3.93359 | 71.4 |

*values ± 0.2°
**values ± 0.2 Å
***values ± 0.5%

Another subject matter of the invention is a process for the manufacture, production, isolation and/or purification of a salt of formula (I) of a molecule of formula (A), in particular in the crystalline form or via a crystallization, this process comprising the following stages:

Use is made of the compound of formula (A) obtained by any process of the prior art. Camphorsulfonic acid in an equimolar amount is then added to this compound (A), so as to form the salt (I). It is possible, for example, to use the precursor 2-substituted quinoline compound (A) prepared by the process described in WO 93/07125 and to form the corresponding salt (I) by addition of camphorsulfonic acid in an equimolar amount.

The compound of formula (I) is then dissolved in a solvent chosen from acetone, methyl ethyl ketone, diethyl ketone, methanol, ethanol, propanol, isopropanol, ethyl ether or diisopropyl ether, at a concentration ranging from 0.05 to 60 g/l.

The solvent is advantageously brought to reflux and then the solution is cooled down to a temperature of between −30° C. and 30° C., in particular between 0 and ambient temperature, for example 20 to 25° C.

The solution can advantageously be seeded during the cooling stage, advantageously when it is at a temperature of between 0 and 4° C.

The crystals obtained are advantageously filtered off and optionally washed with diisopropyl ether.

The choice of the crystallization solvent or of the mixture of crystallization solvents and of the cooling rate can result in different crystalline forms for the same molecule.

In the case of 2-(n-propyl)quinoline, it is advantageously planned to dissolve it in a mixture of methanol and ethyl ether. An equimolar amount of camphorsulfonic acid is subsequently added and heating is carried out to reflux of the solvent. Subsequently, cooling is allowed to take place and a few drops of diisopropyl ether are added.

The camphorsulfonic acid salt of 2-substituted quinoline thus obtained is obtained in the form of homogeneous crystals from white to slightly beige in color. If desired, the product of formula (I), once crystallized, can be ground and/or sieved and/or granulated in combination with excipients, for example by the dry route by a compacting stage, in order to be provided in the form of a powder which is perfectly homogeneous for the purpose of the formulation thereof.

The physical properties of the salt of formula (I) make possible its pharmaceutical formulation in a solid formulation form of hard gelatin capsule or tablet type or also in the form of powders, in particular for reconstitution at the time of use of a solution or suspension with a uniform and reproducible composition. The crystalline form of a salt of formula (I) thus obtained is stable on storage, even under high temperature and humidity conditions, such as those of tropical climates.

A further subject matter of the invention is any pharmaceutical composition comprising this salt of formula (I), in particular in its crystalline form or in one of its crystalline forms, and a pharmaceutical vehicle, in particular with one or more nontoxic inert excipients suited to the pathology, to the population to be treated and to the climatic conditions.

Mention may be made, among the pharmaceutical compositions which can be produced from the salts of formula (I) which are subject matters of the invention, of those which make possible oral, parenteral or nasal administration, tablets (simple or sugar-coated), sublingual tablets, hard gelatin capsules, tablets, suppositories, creams, ointments, injectable preparations, suspensions to be taken orally, and the like.

The dosage is adjusted according to the pathology to be treated, the severity of the condition, the age and weight of the patient and the administration route. It can vary from 0.01 to 50 mg per day in one or more administrations.

Another subject matter of the invention is a molecule of formula (I) for the use thereof in the prevention or treatment of a disease selected from infections due to protozoa and infections due to retroviruses, in particular a disease selected from HIV, HTLV, leishmaniosis, trypanosomiasis or toxoplasmosis.

Another subject matter of the invention is the use of a salt of formula (I) in the preparation of a medicament intended for the prevention or treatment of a disease selected from infections due to protozoa, such as leishmaniosis, trypanosomiasis or toxoplasmosis, and/or infections due to retroviruses, such as, for example, HIV or HTLV.

Experimental Part

1—Preparation of the camphorsulfonic salt of 2-(n-propyl)quinoline

The 2-(n-propyl)quinoline was prepared in accordance with the procedure taught by WO 93/07125.

The 2-(n-propyl)quinoline thus obtained (6.5152 g) is in the form of an oil. It is dissolved in 20 ml of methanol and 60 ml of ether at 20° C. 8.8 g of camphorsulfonic acid are then added to the solution with stirring and gentle heating is carried out with stirring.

Cooling is allowed to take place and a few drops of diisopropyl ether are added, and the precipitation of crystals is observed, which crystals are filtered off and washed with diisopropyl ether.

2—Characterization

The crystals thus obtained (12.7439 g) are characterized by optical microscopy and by X-ray diffraction.

A—Optical Microscopy

Crystals of 2-(n-propyl)quinoline camsylate are observed in FIG. 1. It concerns optical microscopy photographs of crystals of camsylate salt in reflected light, magnification×40.

Figure 2:
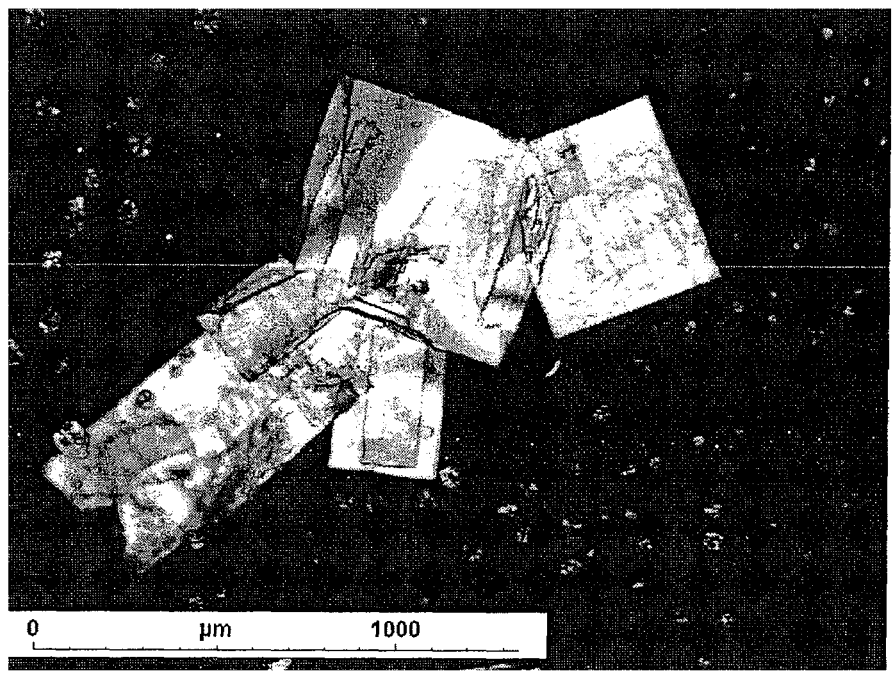
FIG. 2 is an optical microscopy photograph of crystals of 2-(n-propyl)quinoline camsylate in polarized light at magnification ×81.

Crystals of 2-(n-propyl)quinoline camsylate are observed in FIG. 2. It concerns optical microscopy photographs of crystals of camsylate salt in polarized light, magnification×81.

B—X-Ray Diffraction

Equipment and Method

The analysis is carried out on a Bruker AXS diffractometer, model D8 Advance, in theta-theta configuration, equipped with a copper anticathode, with a sample holder made of monocrystalline silicon and with a linear detector having spatial localization.

First, the samples are deposited on the silicon support without prior treatment or trituration and the diffractograms are recorded according to the conditions presented in table 1.

TABLE 1

Instrumental operating conditions for the acquisition of the X-ray diffraction profiles

| Temperature | | | Ambient |
|---|---|---|---|
| Atmosphere | | | Ambient |
| X-ray generator | voltage (kV) | | 40 |
| | strength (mA) | | 40 |
| X-ray source | target | | Cu |
| | emission line: | $K\lambda_1$ (nm) | 0.15406 |
| | | $K\lambda_2$ (nm) | 0.15444 |
| | | ratio $K\lambda_2:K\lambda_1$ | 0.5 |
| | $K\beta$ line filter | | Ni |
| Slit (mm) | antidivergence | | 0.6 |
| Goniometer | angular sector scanned (° in 2θ) | | 4-70 |
| | displacement step (° in 2θ) | | 0.069 |
| Rotational speed of the sample holder (rpm) | | | 30 |
| Detection | angular aperture (°) | | 8 |
| | exposure time per goniometer step (s) | | 6 |

Results

Figure 3:
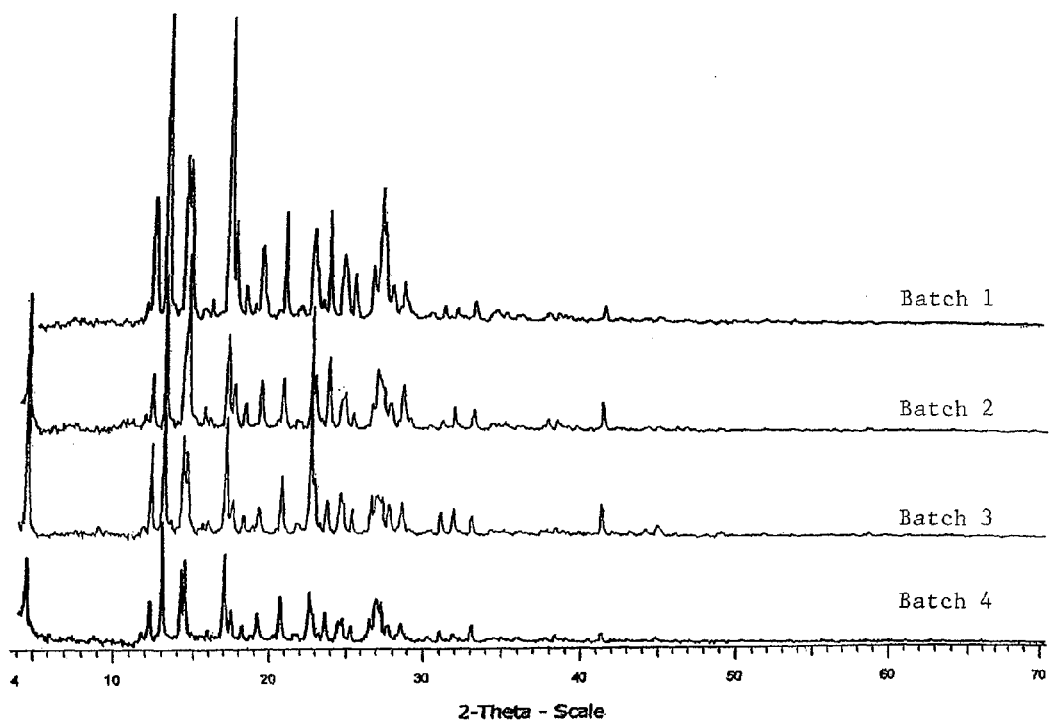
FIG. 3 is the superimposition of X-ray diffraction profiles of four batches of camsylate salt crystals that are in accordance with the present invention.

The experiment is carried out on four separate batches of product numbered 1 to 4. The superimposition of the X-ray diffraction profiles of the four batches is represented in FIG. 3. Diffraction lines are present in each of the diffractograms of the batches analyzed, indicating the presence of crystallized material, and no amorphous phase is detected. The presence of the same crystalline phase is found in the four batches.

Figure 5:
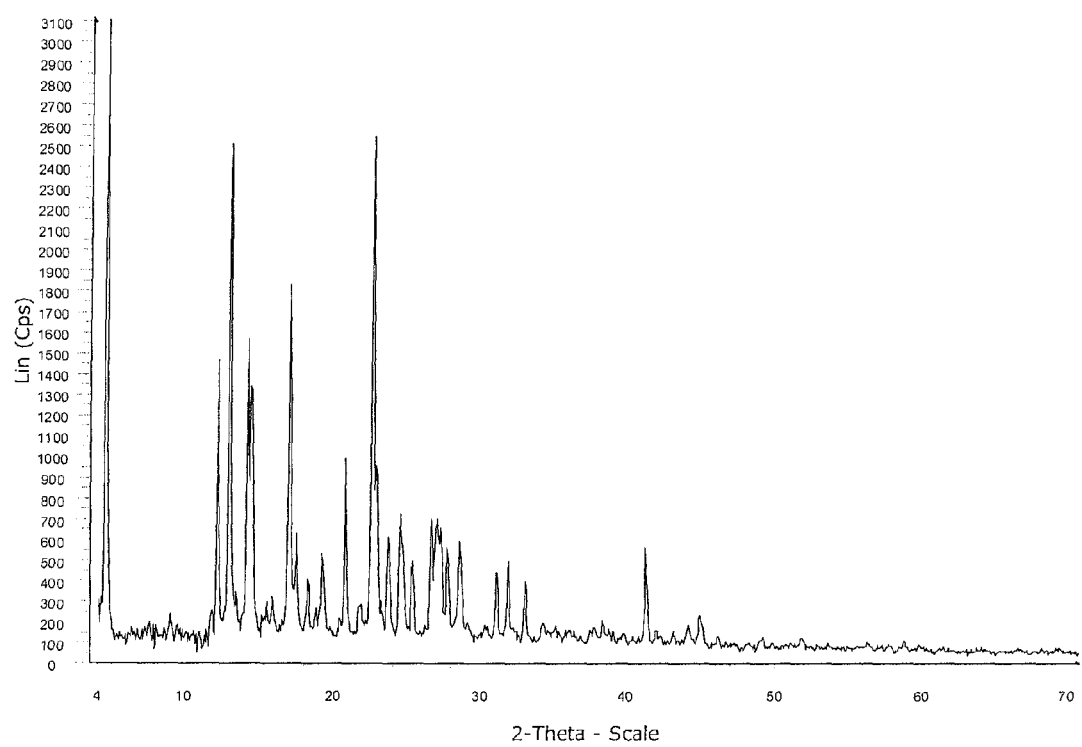
FIG. 5 is a powder X-ray diffraction profile of one of the camsylate salt batches shown in FIG. 3.

The powder X-ray diffraction profile of the camsylate salt of one of the batches is illustrated in a more detailed fashion in FIG. 5. The profile corresponds to table 2 below, in which the list of the powder X-ray diffraction peaks of the camsylate salt is summarized.

TABLE 2

List of the powder X-ray diffraction peaks of the camsylate salt of 2-(n-propyl)quinoline

| 2-Theta angle (°) | Interlattice distance d (angstrom) | Intensity (Cts) | Relative intensity (%) |
|---|---|---|---|
| 4.463 | 19.78297 | 2063 | 79.1 |
| 7.513 | 11.75803 | 196 | 7.5 |
| 8.64 | 10.22599 | 151 | 5.8 |
| 10.352 | 8.53876 | 241 | 9.3 |
| 11.808 | 7.48837 | 326 | 12.5 |
| 12.164 | 7.27052 | 917 | 35.1 |
| 12.975 | 6.81756 | 2329 | 89.3 |
| 14.223 | 6.22226 | 1295 | 49.6 |
| 14.407 | 6.14309 | 2609 | 100 |

TABLE 2-continued

List of the powder X-ray diffraction peaks of the camsylate salt of 2-(n-propyl)quinoline

| 2-Theta angle (°) | Interlattice distance d (angstrom) | Intensity (Cts) | Relative intensity (%) |
|---|---|---|---|
| 15.548 | 5.69468 | 445 | 17 |
| 15.899 | 5.5697 | 276 | 10.6 |
| 17.02 | 5.20542 | 1479 | 56.7 |
| 17.452 | 5.07755 | 769 | 29.5 |
| 18.151 | 4.88352 | 489 | 18.8 |
| 19.247 | 4.60779 | 812 | 31.1 |
| 20.354 | 4.35972 | 242 | 9.3 |
| 20.697 | 4.28815 | 842 | 32.3 |
| 21.604 | 4.11004 | 234 | 9 |
| 22.586 | 3.93359 | 1864 | 71.4 |
| 22.885 | 3.88283 | 886 | 34 |
| 23.168 | 3.83615 | 262 | 10.1 |
| 23.66 | 3.75743 | 1152 | 44.2 |
| 24.592 | 3.6171 | 591 | 22.7 |
| 24.707 | 3.6005 | 641 | 24.6 |
| 25.298 | 3.5177 | 353 | 13.5 |
| 26.218 | 3.39633 | 170 | 6.5 |
| 26.631 | 3.34457 | 467 | 17.9 |
| 26.978 | 3.30231 | 982 | 37.6 |
| 27.217 | 3.27392 | 796 | 30.5 |
| 27.697 | 3.21819 | 478 | 18.3 |
| 28.55 | 3.12402 | 743 | 28.5 |
| 28.994 | 3.07712 | 268 | 10.3 |
| 30.352 | 2.94248 | 168 | 6.4 |
| 31.079 | 2.87526 | 226 | 8.7 |
| 31.894 | 2.80364 | 416 | 15.9 |
| 32.397 | 2.76125 | 155 | 6 |
| 33.07 | 2.7066 | 389 | 14.9 |
| 34.3 | 2.61232 | 184 | 7.1 |
| 34.607 | 2.58981 | 181 | 7 |
| 35.041 | 2.55872 | 198 | 7.6 |
| 35.809 | 2.5056 | 161 | 6.2 |
| 37.751 | 2.38103 | 239 | 9.2 |
| 38.388 | 2.34298 | 225 | 8.6 |
| 39.063 | 2.30406 | 144 | 5.5 |
| 39.54 | 2.27734 | 145 | 5.5 |
| 40.521 | 2.22446 | 110 | 4.2 |
| 41.294 | 2.18455 | 489 | 18.7 |
| 42.282 | 2.13578 | 121 | 4.6 |
| 42.604 | 2.1204 | 119 | 4.6 |
| 43.112 | 2.09658 | 106 | 4.1 |
| 44.276 | 2.04412 | 135 | 5.2 |
| 44.945 | 2.01525 | 136 | 5.2 |
| 46.119 | 1.96664 | 130 | 5 |
| 46.789 | 1.94 | 120 | 4.6 |
| 48.358 | 1.88066 | 87 | 3.3 |
| 48.893 | 1.86132 | 105 | 4 |
| 51.81 | 1.76319 | 93.7 | 3.6 |
| 56.362 | 1.6311 | 81.4 | 3.1 |
| 58.642 | 1.573 | 80.7 | 3.1 |

C—Hygroscopicity

Equipment and Method

The hygroscopicity of the 2-(n-propyl)quinoline camsylate crystals is evaluated by studying the sorption/desorption isotherm of water in the vapor phase on a device of DVS-1000 type sold by SMS.

The sample, analyzed in a quartz pan with a specimen size of the order of 10 mg, is subjected to two cycles of variation in relative humidity (RH) which are linked together continuously. Each cycle comprises two stages, adsorption and then desorption of water, during which the relative humidity in the measuring chamber is increased and then decreased gradually according to the conditions described in table 2.

Figure 4:
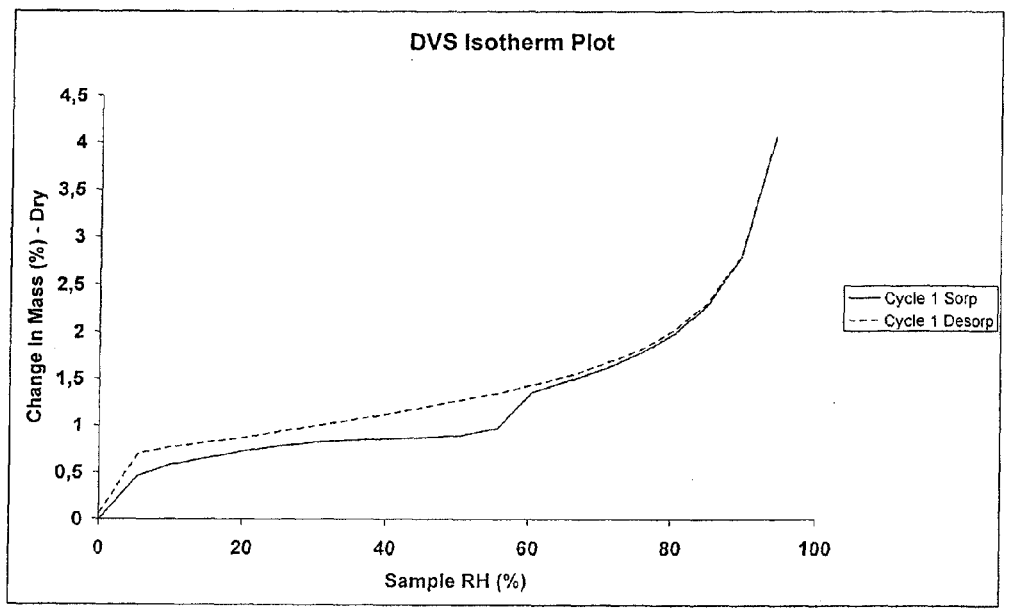
FIG. 4 shows the isotherms of the camsylate salt crystals for adsorption and for desorption of water at 25° C.

The sample is first dried under a stream of filtered dry air until its weight has stabilized. The stages of adsorption and of desorption are then made successively. The carrier gas used to maintain the relative humidity at a set percentage is air dried upstream of the device and delivered at a flow rate of 100 ml/min. During the progression of the program, the temperature in the measuring chamber is maintained at 25° C.
Results The isotherms for adsorption and for desorption of water at 25° C. are represented in FIG. 4.

This sorption/desorption isotherm, carried out at 25° C., shows an increase in weight of less than 2% at 25° C./60% relative humidity, in comparison with the weight of the product equilibrated at 0% relative humidity at 25° C.

D—Chemical Stability

Preparation and Preservation of the Solutions

The quinoline salts are dissolved at a concentration of 200 µg/ml in five different solvents: methanol, an aqueous solution buffered at pH 7, an aqueous camphorsulfonic acid solution at pH 2, dimethyl sulfoxide (DMSO) and an aqueous solution comprising a mixture of carboxymethylcellulose at 0.5% and Tween 80 at 0.5%.

Each preparation is divided into three parts which are stored under different conditions of temperature and of luminosity: at 4° C., at ambient temperature under the influence of light and at ambient temperature with the exclusion of light. The samples are diluted (1:20) and then analyzed by high performance liquid chromatography (HPLC) daily for 9 days.

Use was made, in carrying out the high performance liquid chromatography analysis, of a Waters LC system comprising a model 600 pump with inline degassing and, as detector, a 996 photodiode detector device. The acquisition of the data was carried out by the use of the Empower® program (Waters, France). The column used was a Symmetry Shield RP18, 3.5 µm 4.6×150 mm. The isocratic mobile phase was used to determine the percentage of the quinolines with, as solvent, a mixture of solution, buffered at pH 4, of acetate and of methanol (40/60 v/v); a flow rate of 1 ml/min at 35° C. was used for the elution. The UV absorbance spectra were recorded at between 210 and 400 nm. The chromatogram of the propyl salt was recorded at 233 nm and that of the alcohol derivative at 249 nm.

Results

It is found that the propyl salt is stable whatever the conditions tested.

The 2-(n-propyl)quinoline in the form of the camphorsulfonic acid salt exhibits a chemical stability compatible with the development of a medicament.

E—Acute Toxicity

Preparation of the Emulsions and Administration of the Quinoline Salts 250 mg of carboxymethylcellulose are dissolved in 50 ml of a 5% glucose solution. 5 ml aliquots containing 0.5% of Tween 80 are emulsified with the quinoline salts (final concentrations at 0.4 mg/ml, 4 mg/ml and 40 mg/ml). The emulsions are subsequently homogenized. The emulsions are administered by force feeding in a single dose to four groups of five female CD-1 mice at the concentrations of 10 mg/kg, 100 mg/kg and 1000 mg/kg and without compounds (control group). The control group receives a glucose-comprising emulsion containing 0.5% of carboxymethyl-cellulose (CMC) and 5% of Tween 80. The behavior of the animals is observed and the number of deaths is counted after 1 min, 15 min, 30 min, 1 h, 4 h, 8 h and each day for 14 days. On the final day, a blood sample is taken. Biochemical analyses are carried out in order to evaluate the nephrotoxicity and the hepatotoxicity, the levels of creatinine, of aspartate aminotransferase (ASAT), of alanine aminotransferase (ALAI) and of cholesterol being quantitatively determined.

Results

In accordance with the results appearing in tables 3 and 4, no signs of irreversible toxicity can be demonstrated at 1 g/kg.

TABLE 3

| | Acute toxicity | | |
|---|---|---|---|
| Compound | No. of animals | Single dose (oral route) | |
| Camphorsulfonate salt of 2-(n-propyl)quinoline | 5 | 1 g/kg | t15 min = 3 mice showed signs of lethargy |
| | | | t1 h = 2 lethargic mice |
| | | | t4 h = absence of toxicity |
| | | 100 mg/kg | absence of toxicity |
| | | 10 mg/kg | absence of toxicity |
| Camphorsulfonate salt of 2-(hydroxyprop-2-enyl)quinoline | 5 | 1 g/kg | t15 min - 1 mouse had bristling hair |
| | | | t1 h - absence of toxicity |
| | | 100 mg/kg | absence of toxicity |
| | | 10 mg/kg | absence of toxicity |
| Control | | CMC/Tween | absence of toxicity |

TABLE 4

| | | Biochemical parameters | | | |
|---|---|---|---|---|---|
| Compound | Dose | Creatinine (µM) | Cholesterol (mM) | ASAT (IU/l) | ALAT (IU/l) |
| Camphorsulfonate salt of 2-(n-propyl)quinoline | 1 g/kg | <18 | 3.8 ± 0.4 | 422 ± 187 | 199 ± 89 |
| | 100 mg/kg | <18 | 4.1 ± 0.5 | 515 ± 72 | 168 ± 67 |
| | 10 mg/kg | <18 | 3.9 ± 0.3 | 410 ± 57 | 215 ± 123 |
| Camphorsulfonate salt of 2-(hydroxyprop-2-enyl)quinoline | 1 g/kg | 20.7 ± 3.1 | 3.4 ± 0.6 | 388 ± 70 | 260 ± 131 |
| | 100 mg/kg | <18 | 4.6 ± 0.5 | 397 ± 202 | 247 ± 76 |
| | 10 mg/kg | <18 | 3.9 ± 0.3 | 337 ± 80 | 223 ± 74 |
| Control | CMC/Tween | <18 | 3.5 ± 0.5 | 456 ± 276 | 304 ± 25 |

3—Formulation

A hard gelatin capsule is prepared using the following ingredients: camphorsulfonic salt of 2-(n-propyl)quinoline, lactose, hydroxypropylmethylcellulose, silica and magnesium stearate.

What is claimed is:

1. A camphorsulfonic acid salt of 2-(n-propyl)quinoline, in the crystalline form, characterized by the presence of the following peaks in the X-ray diffraction spectrum, measured on a diffractometer in theta-theta configuration, equipped with a copper anticathode and expressed in terms of interlattice distances d, of Bragg 2-theta angle and of relative intensity:

| 2-Theta angle (°)* | Interlattice distance d (angström)** | Relative intensity (%)*** |
|---|---|---|
| 4.463 | 19.78297 | 79.1 |
| 12.975 | 6.81756 | 89.3 |
| 14.223 | 6.22226 | 49.6 |
| 14.407 | 6.14309 | 100 |
| 17.02 | 5.20542 | 56.7 |
| 22.586 | 3.93359 | 71.4. |

*values ± 0.2°
**values ± 0.2 Å
***values ± 0.5%

2. A process for the manufacture of the crystalline form of a camphorsulfonic acid salt of 2-(n-propyl) quinoline as claimed in claim 1, this process comprising a stage of addition of camphorsulfonic acid in equimolar amounts to the compound (A):

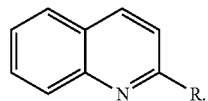
(A)

3. The process as claimed in claim 2, comprising at least the following stages:
dissolving camphorsulfonic acid salt of 2-(n-propyl) quinoline in a solvent chosen from acetone, methyl ethyl ketone, diethyl ketone, methanol, ethanol, propanol, isopropanol, ethyl ether or diisopropyl ether, at a concentration ranging from 0.05 to 60 g/l to form a solution,
bringing the solution to reflux; and
cooling the solution to a temperature of between −30° C. and 30° C.,
filtering the solution to obtain crystals and optionally washing the crystals.

4. The process as claimed in claim 3, for the production of the camphorsulfonic salt of 2-(n-propyl)quinoline, comprising at least the following stages:
dissolving 2-(n-propyl)quinoline in a mixture of methanol and ethyl ether,
adding an equimolar amount of camphorsulfonic acid,
heating is carried out to reflux of the solvent,
cooling is allowed to take place, and
adding a few drops of diisopropyl ether.

5. A medicament which comprises a camphorsulfonic acid salt of 2-(n-propyl) quinoline as claimed in claim 1 and a pharmaceutical vehicle.

6. The medicament as claimed in claim 5, which is in the form of a tablet, of a hard gelatin capsule or of a powder.

* * * * *

UNITED STATES PATENT AND TRADEMARK OFFICE
CERTIFICATE OF CORRECTION

PATENT NO. : 8,344,145 B2
APPLICATION NO. : 12/937878
DATED : January 1, 2013
INVENTOR(S) : Fournet et al.

It is certified that error appears in the above-identified patent and that said Letters Patent is hereby corrected as shown below:

Column 8,
Line 13, "ALAI" should read --ALAT--.

Signed and Sealed this
Nineteenth Day of March, 2013

Teresa Stanek Rea
*Acting Director of the United States Patent and Trademark Office*